United States Patent [19]

Hasson

[11] Patent Number: 4,617,933
[45] Date of Patent: Oct. 21, 1986

[54] LAPAROSCOPE CANNULA WITH IMPROVED SUTURE RECEIVING MEANS

[76] Inventor: Harrith M. Hasson, 345 Fullerton Pky., Chicago, Ill. 60614

[21] Appl. No.: 122,240

[22] Filed: Feb. 19, 1980

[51] Int. Cl.$^4$ ............................................. A61M 25/00
[52] U.S. Cl. ................................. 128/348.1; 128/335
[58] Field of Search ................... 128/347, 348, 334 R, 128/334 C, 327, 335, 335.5, DIG. 32, 348.1; 3/13; 24/264

[56] References Cited

U.S. PATENT DOCUMENTS

| | | | |
|---|---|---|---|
| 4,520 | 8/1871 | Cooley | 24/264 U X |
| 1,547,677 | 7/1925 | Ouellet | 24/264 U X |
| 2,246,229 | 6/1941 | Wohlmuth | 24/264 U X |
| 3,817,251 | 6/1974 | Hasson | 128/348 |
| 3,831,608 | 8/1974 | Kletschka et al. | 128/335 |
| 3,877,434 | 4/1975 | Ferguson et al. | 128/327 |
| 3,910,281 | 10/1975 | Kletschka et al. | 128/335 |
| 3,931,821 | 1/1976 | Kletschka et al. | 128/335 |
| 4,185,636 | 1/1980 | Gabbay et al. | 128/334 R |

FOREIGN PATENT DOCUMENTS 1102994 2/1968 United Kingdom ............... 128/347

Primary Examiner—Robert A. Hafer
Assistant Examiner—Arnold W. Kramer
Attorney, Agent, or Firm—George H. Gerstman

[57] ABSTRACT

A laparoscope cannula including four rigid members extending from the cannula for receiving sutures to maintain the cannula in place with respect to the patient's abdomen. Each of the rigid members defines a slot which opens to the outside and tapers inwardly toward the cannula. The rigid members extend parallel to the axis of the cannula and are fixed to gas valve means carried by the cannula.

2 Claims, 4 Drawing Figures

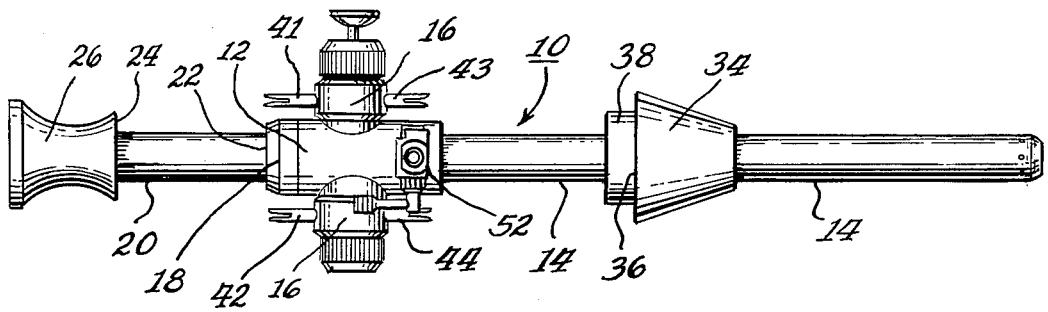
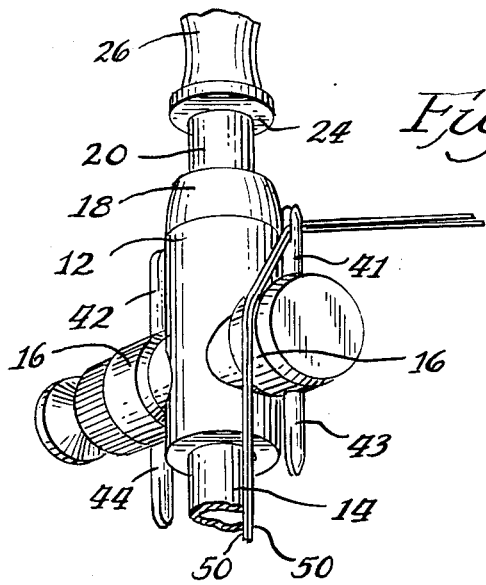
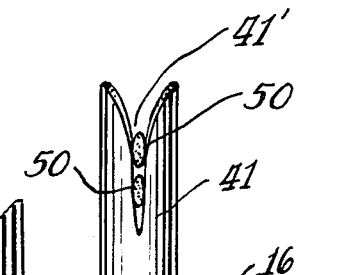
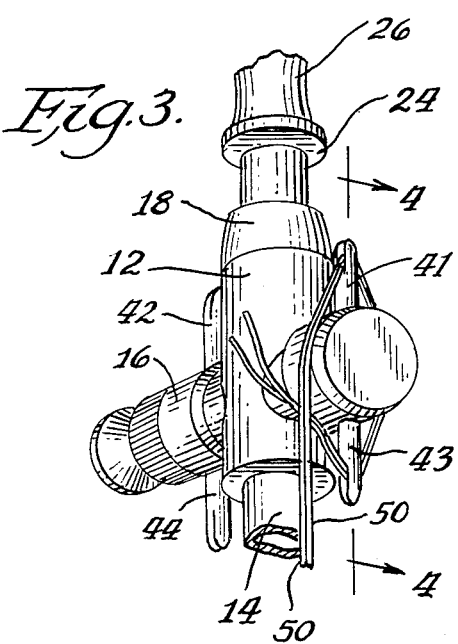
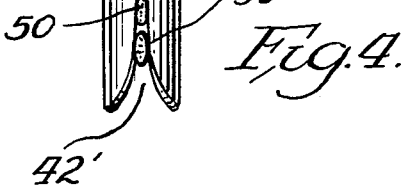

LAPAROSCOPE CANNULA WITH IMPROVED SUTURE RECEIVING MEANS

BACKGROUND OF THE INVENTION

The laparoscope (peritoneoscope, celioscope) is an important tool of modern gynecologic diagnosis and surgical treatment. A prior art technique of laparoscopy requires the intoductidn of a needle into the peritoneal cavity to establish a pneumoperitoneum, and the abdominal wall is then punctured with a cannula, bearing a sharp trochar. Both of these steps are performed blindly, and there is thus the possibility of accidentally puncturing a vital organ or a blood vessel. The trochar is subsequently withdrawn, and the lighted laparoscope is inserted through the cannula into the peritoneal cavity for visualization.

Another technique of performing laparoscopy is discussed in my article in the *American Journal of Obstetrics and Gynecology*, St. Louis, Vol. 110, No. 6, pages 886–887, July 15, 1971. In this technique, a laparoscope cannula with a trumpet valve is fitted with a thin, cone-shaped steel sleeve, mounted on the cannula's shaft. The cone sleeve may be fitted with an extender to accommodate variations in the thickness of the abdominal wall and in the distance between the umbilicus and the symphysis pubis.

The purpose of the conical sleeve is to seal the peritoneal and fascial gap, by advancing the cone deeper through the incisional opening. Although the use of such a cannula has been found generally satisfactory, certain problems were noted. These problems included the occasional occurrence of gas leaks, the need for an assistant to hold the cannula in place while the scope was being withdrawn or manipulated, and the need to use several cannulas of different sizes to accommodate individual variations in the thickness of the abdominal wall.

In my U.S. Pat. No. 3,817,251, issued June 18, 1974, I disclosed a laparoscope cannula which alleviated the aforementioned problems by utilizing a generally truncated cone-shaped sleeve which is adjustably positioned on the distal shaft portion and by utilizing hooks carried by the cannula for receiving a suture, to maintain the cannula in place with respect to the patient's abdomen.

It has been found, however, that the hooks are difficult for some persons to utilize because on occasion the suture may loosen if the suture is not tied properly. Further, the degree of tension is unpredictable, thereby leading to possible escape of the gas because the sleeve may not be in a snug position within the fascia. Further, with the use of hooks, it is necessary to tie a knot with the suture and the tying of the knot may result in the breaking of the suture if excessive tension is applied. Still further, the tying of the knot may take some persons a relatively long time and thus become inefficient in actual practice.

The present invention is an improvement upon the laparoscope cannula disclosed in my U.S. Pat. No. 3,817,251, in that it provides novel suture-receiving means that significantly alleviate the problems concomitant with the use of hooks.

BRIEF DESCRIPTION OF THE INVENTION

In accordance with the present invention, a laparoscope cannula is provided comprising a proximal shaft portion forming an inlet to receive a blunt obturator and a laparoscope. The cannula includes a distal shaft portion for insertion into the abdominal cavity of a patient. Gas valve means couple the proximal shaft portion and the distal shaft portion. An adjustable sleeve is positioned on the distal shaft portion, and rigid means carried by the cannula are provided for receiving a suture to maintain the cannula in place with respect to the patient's abdomen.

The invention is characterized in that the suture-receiving means comprises a rigid member extending from the cannula and defining a slot which opens to the outside and tapers inwardly toward the cannula. The rigid member is fixed at one end thereof to the cannula and is adapted to grasp sutures between opposed walls defining the slot.

In the illustrative embodiment, first, second, third and fourth rigid members are provided, with the second rigid member extending from the cannula on an opposite side from the first rigid member and with the fourth rigid member extending from the cannula on a opposite side from the third rigid member. The first and third rigid members are coaxial and the second and fourth rigid members are coaxial. Each of the rigid members defines a slot which opens to the outside and is adapted to grasp sutures between opposed walls defining the slot.

A more detailed explanation of the invention is provided in the following description and claims, and is illustrated in the accompanying drawings.

BRIEF DESCRIPTION OF THE DRAWINGS

FIG. 1 is a front elevation of a laparoscope cannula constructed in accordance with the principles of the present invention, showing a blunt obturator extending into the proximal shaft portion;

FIG. 2 is a perspective view of the suture-receiving means of the present invention, showing the sutures being attached initially;

FIG. 3 is a perspective view similar to the view of FIG. 2, but showing the sutures in a more complete attachment mode; and FIG. 4 is a greatly enlarged elevational view of two of the rigid members of the suture-receiving means, taken along the plane of the line 4—4 of FIG. 3.

DETAILED DESCRIPTION OF THE ILLUSTRATIVE EMBODIMENT

Referring to FIG. 1 in particular, the cannula 10 shown therein includes a proximal shaft portion 12, a distal shaft portion 14, and gas valve means 16 which couple the proximal shaft portion 12 and the distal shaft portion 14. The shaft portions 12 and 14 are preferably stainless steel or chrome-plated steel. Gas valve means 16 comprises a trumpet valve conventionally used in laparoscope cannulas.

The front of proximal shaft portion 12 comprises a rubber inlet 18 which defines a central opening that is no smaller than the external diameter of a conventional blunt obturator 20. The front end 22 of inlet 18 is of a size to provide an abutting relationship with end 24 of handle 26 of blunt obturator 20.

A sleeve 34, in the form of a truncated cone, is provided on distal shaft portion 14 and is slidable with respect thereto. Sleeve 34 is preferably formed of stainless steel or chrome-plated steel, with the base 36 facing the proximal shaft portion 12. A rubber washer-type member 38 is connected to the sleeve 34, to achieve a snug, frictional fit with respect to the outer surface of distal shaft 14. Sleeve 34 may be locked in place in the manner described in U.S. Pat. No. 3,817,251 or a set screw type means may be utilized, if desired.

Rigid means are carried by the cannula for receiving a suture to maintain the cannula in place with respect to the patient's abdomen. The suture-receiving means comprises a first rigid member 41 extending from the gas valve means 16, a second rigid member 42 extending from the gas valve means 16, a third rigid member 43 extending from the gas valve means 16 and a fourth rigid member 44 extending from the gas valve means 16. Each of the members 41, 42, 43 and 44 has one end fixed to the gas valve means 16, preferably by means of internal threads which cooperate with the external threads of bolts that are attached to gas valve means 16.

It can be seen that rigid members 41 and 43 are coaxial, and that rigid members 42 and 44 are coaxial, with coaxial member 41, 43 positioned on the opposite side of gas valve means 16 from coaxial rigid members 42 and 44. Referring to FIG. 4 in particular, it can be seen that rigid member 41 defines a slot 41' which opens to the outside and tapers inwardly toward gas valve means 16. Likewise, rigid members 43 defines a slot 43' which opens to the outside and tapers inwardly toward gas valve means 16. In the same manner, second rigid member 42 and fourth rigid member 44 also define similar slots, as illustrated in FIGS. 1-3.

The opposed walls which define the slots of the rigid members are dimensioned to receive and hold a suture therein. As illustrated in FIG. 2, the two ends of a suture 50 brought up from the patient are inserted into slot 41' and FIG. 3 illustrates how the suture is locked in place by bringing it around gas valve means 16 and into slot 43'. The tapered shape of the slot enables sutures having different gauges (diameters) to be held in place by wedging between the walls defining the slots. There is no need to tie a knot because the suture effectively locks in place because of the grasping effect resulting from the tapered construction.

Although suture 50 is illustrated in FIG. 3 in connection with rigid members 41 and 43, another suture would also be taken from the patient and likewise connected to rigid members 42 and 44. As illustrated, the rigid members are symmetrical with respect to the cannula and a taut connection of the sutures to both of the coaxial sets of rigid members maintains the cannula in place in a balanced manner. Thus there is no need for an assistant to hold the cannula in place when the scope is manipulated.

The operation is performed in the following manner. General anesthesia with endotracheal intubation is employed. A small curvilinear incision, two to four centimeters long, is made through the skin of the anterior abdominal wall 0.5 to 1 centimeter below the lower edge of the umbilical fossa. The skin edges are retracted with two Allis clamps, then with a set of two small retractors. The subcutaneous adipose tissues are reflected to expose the linea alba.

Dissection is carried out mostly bluntly with the handle of the knife, sweeping the adipose tissues inferiorly, away from the umbilicus. The exposed deep fascia is then grasped with two Kocher clamps placed side by side transversely. The fascia is held forcibly upwards and incised transversely, for approximately 1.5 centimeters, a short distance below the aponeurotic umbilical ring. Two sutures are passed, one through each fascial edge, and tagged. The fascial sutures are held upwards and apart, and two retractors are placed laterally inside the fascial incision, creating a system of four-way retraction.

At this point, the properitoneal layer of adipose tissue can be clearly viewed in most multiparous women. However, in many patients, usually nulliparous, a distinct fascial layer is present which has to be incised to expose the properitoneal adipose layer.

Blunt dissection of the adipose tissue followed by thrusting a small hemostat against the peritoneum is usually sufficient to create an opening in the peritoneal cavity. Occasionally, however, the peritoneum has to be picked up and incised because of increased tensile strength.

A clear, adequate opening in the peritoneum, confirmed by viewing the small bowel and/or the omentum, is a useful step in the procedure. The peritoneal opening should be over one centimeter in diameter. The cannula 10 is then readied by fixing the sleeve 34 in position depending upon the thickness of the abdominal wall.

One edge of the peritoneum is held with a small hemostat to guide the cannula 10 carrying the blunt obturator 20 as it is inserted through the opening into the peritoneal cavity. The hemostat is then removed, allowing the peritoneal defect to slide freely downwards, as the cannula is placed through the abdominal wall in an obliquely slanted position. Alternatively, two small retractors may be placed inside the peritoneal defect and the cannula 10 inserted through the opening between the retractors. If the cannula is not guided in its peritoneal insertion, it may slip away from the peritoneal opening into the properitoneal space.

The retractors are removed and the ends of the fascial sutures are pulled snugly into the rigid members as illustrated in FIGS. 2 and 3, with the suture ends first being pulled into the upper rigid members 41 and 42 (FIG. 2) and then into lower rigid members 43 and 44 for secure locking. This maneuver pulls the fascia firmly against sleeve 34 and provides an airtight seal. Thus escape of the gas is prevented.

The fixed sutures also maintain the cannula in position, preventing movement of the cannula during manipulation of the laparoscope. It is important to stabilize the cannula downward while pulling the fascial sutures into the rigid members to prevent displacement of the cannula. Gas is insufflated through the valve 52 of the cannula to create a pneumoperitoneum. Insufflation is initiated while the sutures are being fixed. The blunt obturator 20 is withdrawn to permit a more rapid flow of gas.

With the establishment of an adequate pneumoperitoneum the lighted laparoscope is introduced, and the procedure continues as usual. When laparoscopy is completed, the instrument is withdrawn, the cavity deflated and the abdominal wall closed in layers.

It is seen that a device has been provided which does not require that the sutures be tied and the rigid members enable a rapid, secure connection.

Although an illustrative embodiment of the invention has been shown and described, it is to be understood that various modifications and substitutions may be made by those skilled in the art without departing from the novel spirit and scope of the present invention.

What is claimed is:

1. A laparoscope cannula comprising a proximal shaft portion forming an inlet to receive a blunt obturator and a laparoscope, a distal shaft portion for insertion into the abdominal cavity of a patient, gas valve means coupling the proximal shaft portion and the distal shaft portion, an adjustable sleeve positioned on the distal shaft portion, and rigid means carried by the cannula for receiving a suture to maintain the cannula in place with respect to the patient's abdomen; characterized in that the suture-receiving means comprises first, second, third and fourth rigid members extending from the cannula, with each of said four rigid members defining a slot which opens to the outside and tapers inwardly toward the cannula, each of said rigid members being fixed at one end thereof to the cannula and being adapted to grasp sutures between opposed walls defining the respective slot, said second and fourth rigid members extending from the cannula on an opposite side from said first and third rigid members, with the four rigid members being symmetrical with respect to the distal shaft portion, said third rigid member being positioned coaxial with said first rigid member and said fourth rigid member being positioned coaxial with said second rigid member, said rigid members extending parallel to the axis of the cannula.

2. A laparoscope cannula as described in claim 1, said rigid members being fixed to said gas valve means.

* * * * *